United States Patent [19]
Burger

[11] Patent Number: 5,843,919
[45] Date of Patent: Dec. 1, 1998

[54] COMPOSITION AND METHOD FOR THE TREATMENT OF ARTHRITIS

[76] Inventor: John A. Burger, 220 10th St., Huntington Beach, Calif. 92648

[21] Appl. No.: 955,098

[22] Filed: Oct. 22, 1997

Related U.S. Application Data

[60] Provisional application No. 60/032,001 Nov. 25, 1996.
[51] Int. Cl.$^6$ .......................... A61K 31/70; A61K 31/20
[52] U.S. Cl. ............................................... 514/62; 514/560
[58] Field of Search ....................................... 514/62, 560

[56] References Cited

U.S. PATENT DOCUMENTS 3,683,076  8/1972  Rovati ..................................... 424/180

OTHER PUBLICATIONS

CA: 123: No. 188030v (Kremer et al.), 1995.

*Primary Examiner*—Theodore J. Criares
*Attorney, Agent, or Firm*—Chernoff, Vilhauer, McLung & Stenzel, LLP; Howard Eisenberg

[57] ABSTRACT

A composition and method for the treatment of arthritis in animals, such as mammals, and a method for making the composition, is disclosed. The composition comprises one or more glucosamines and one or more omega-3-fatty acids and is made by combining an omega-3-fatty acid with a glucosamine.

28 Claims, No Drawings

COMPOSITION AND METHOD FOR THE TREATMENT OF ARTHRITIS

This application claims the benefit of the priority of pending Provisional Application 60/032,001, filed Nov. 25, 1996.

FIELD OF THE INVENTION

The invention pertains to the field of therapeutic agents to control the symptoms of arthritis, such as osteoarthritis.

BACKGROUND OF THE INVENTION

Arthritis is a serious medical condition affecting the joints of humans and domestic animals, such as dogs, cats, horses, and cattle. Osteoarthritis, a chronic degenerative arthritis in which the cartilage of the joint breaks down, is often a sequela of chronic or acute injury to a joint due to any cause such as, for example, trauma, infection, autoimmune disease such as lupus or rheumatoid arthritis, or as a result of wear due to aging. Clinical signs of osteoarthritis can range from mild pain on extension and flexion of a joint to severe pain and disability, up to complete loss of use of the joint or inability to bear weight on an affected limb.

No medical cure exists for osteoarthritis. The progressive degeneration of the joint due to osteoarthritis is irreversible. Present therapies are directed to palliative medical therapies to reduce inflammation and pain and surgical therapies to reconstruct an affected joint or, in severe cases, to replace the joint with an artificial, prosthetic joint.

Presently available medications for the treatment of osteoarthritis include anti-inflammatory compounds such as corticosteroids, and non-steroidal anti-inflammatory drugs such as aspirin, phenylbutazone, and ibuprofen, and pain relievers such as acetaminophen. Medical treatment, other than that directed against the cause of the osteoarthritis, such as antibiotics in the case of infectious osteoarthritis, generally does not alter the progression of the disease or reverse the pathologic changes in the joint.

In recent years, medical treatments for osteoarthritis have been proposed to replace some of the natural constituents of synovial fluid and cartilage which are decreased in the arthritic joint. These constituents include glucosamine or polymers thereof, including hyaluronic acid, chondroitin sulfate, and glycosaminoglycans. Nutritional compounds such as the omega-3-fatty acids have been suggested to have anti-inflammatory properties which may be effective in reducing symptoms of osteoarthritis. An injectable composition containing polysulphated glycosaminoglycan (ADEQUAN®, Luitpold Pharmaceuticals, Shirley, N.Y.) has been reported to be effective in treating the symptoms of osteoarthritis. Little if any success has been reported in treatment of osteoarthritis, however, with glucosamine or omega-3-fatty acids.

Human clinical trials have been performed to evaluate the efficacy of glucosamine in the treatment of arthritis. Although some short-term symptomatic relief was obtained with glucosamine, no evidence of long-term benefit of glucosamine to relieve symptoms or to slow the underlying degenerative disease process was shown. Based on experience with glucosamine for the treatment of arthritis, the Arthritis Foundation (Atlanta, Ga.) has stated that it cannot recommend glucosamine as a treatment for any form of arthritis, including osteoarthritis.

CARTIFLEX® (VRx Pharmaceuticals, Harbor City, Calif.), a non-ethical tablet formulation containing a freeze dried mussel, *Perna canaliculus,* which contains glucosamine, glycosaminoglycans such as chondroitin sulfate, and omega-3-fatty acids, is advertised as a nutritional supplement to provide long-term improvement in arthritis in dogs. No clinical trials of CARTIFLEX® have been reported.

Presently available medical therapies may result in undesirable side effects. The side effects include gastric irritation, for example with aspirin, ibuprofen, and non-steroidal anti-inflammatory drugs, blood dyscrasias, for example with phenylbutazone, prolonged clotting time, for example with aspirin, and various metabolic disorders, for example with steroidal medications.

A need exists for an effective palliative medication for the treatment of osteoarthritis which is both safe and effective when used for both short-term and long-term therapy.

SUMMARY OF THE INVENTION

In accordance with the invention, it has been discovered that a combination therapy of a glucosamine, or a polymer or copolymer thereof, and an omega-3-fatty acid effectively controls symptoms of arthritis and provides relief from the associated pain and discomfort. The relief of symptoms of arthritis due to treatment with the combination therapeutic composition of the invention is much greater than would be expected based on the therapeutic effect of either of the components when administered in the absence of the other. It has been further unexpectedly discovered that the combination therapy has an effectiveness comparable to other presently available medications, such as aspirin, without the undesirable side effects often encountered with these medications.

While not wishing to be bound by theory, it is believed that the therapeutic composition is effective due to the synergistic activity of the two essential components of the composition. It is believed that glucosamine, one of the biochemical components which make up the matrix of mammalian cartilage, is a chondroprotective agent which acts as a competitive inhibitor of inflammatory agents produced by the body which attack the cartilage and/or joint fluid in the joints, and that omega-3-fatty acids are anti-inflammatory compounds which act as competitive inhibitors of the arachidonic acid cascade, which acid is a precursor to the synthesis of prostaglandins which act in mammals to regulate inflammation.

One embodiment of the invention is a therapeutic composition for treating and controlling the symptoms of arthritis, especially osteoarthritis, which composition comprises a glucosamine and an omega-3-fatty acid. In one embodiment, other than glucosamine and omega-3-fatty acids, the composition is free of compounds which are effective in controlling the symptoms of arthritis. Preferably, the glucosamine is selected from the group consisting of glucosamine hydrochloride and glucosamine sulfate, and the omega-3-fatty acid is a combination of eicosapentaenoic acid and docosahexaenoic acid.

Another embodiment of the invention is a method for treating or controlling the symptoms of arthritis, especially osteoarthritis, which method comprises administering to a patient suffering from arthritis a therapeutic composition which comprises a glucosamine and an omega-3-fatty acid. The composition may comprise glucosamine as the sole chondroprotective agent, and/or omega-3-fatty acid as the sole anti-inflammatory agent. Preferably, glucosamine and omega-3-fatty acid are the sole components in the composition which are effective in treating the symptoms of arthritis. In a preferred embodiment, the glucosamine is selected from the group consisting of glucosamine hydrochloride and glucosamine sulfate, and the omega-3-fatty acid is eicosapentaenoic acid and docosahexaenoic acid.

A further embodiment of the invention is a method for making a composition for treating the symptoms of arthritis, especially osteoarthritis, which method comprises obtaining a composition comprising glucosamine, or a polymer or copolymer thereof, which composition is substantially free of omega-3-fatty acid, obtaining a composition comprising an omega-3-fatty acid, which composition is substantially free of glucosamine, and combining the glucosamine composition and the omega-3-fatty acid composition. In a preferred embodiment, the glucosamine and/or the omega-3-fatty acid compositions comprise purified glucosamine and omega-3-fatty acid, respectively.

DETAILED DESCRIPTION OF THE INVENTION

In accordance with the therapeutic composition of the invention, a composition containing or made from a combination of a glucosamine and an omega-3-fatty acid has been discovered to be an effective and safe therapy for arthritis in animals. Animals that may benefit from treatment with the composition include mammals, such as humans and domestic animals, including dogs, cats, horses, and cows.

The glucosamine component may contain any glucosamine or combination of glucosamines. Examples of glucosamines which are suitable for the therapeutic composition of the invention include glucosamine hydrochloride, glucosamine sulfate, and N-acetyl glucosamine (NAG), and homologues and analogues thereof. The glucosamine component may be a polymer or copolymer of a glucosamine, such as hyaluronic acid, keratan sulfate, dermatan sulfate, or a polymer or copolymer of galactosamine, such as chondroitin sulfate. The omega-3-fatty acid component may contain any omega-3-fatty acid or combination of omega-3-fatty acids. Examples of omega-3-fatty acids which are suitable for the therapeutic composition of the invention include eicosapentaenoic acid (EPA) and docosahexaenoic acid (DHA), and homologues and analogues thereof.

The therapeutic composition is preferably in the form of a tablet or a capsule, such as a gel capsule, for oral administration. Preferred liquid formulations for oral administration include solutions and suspensions. Any form of the composition is suitable which allows for delivery of effective amounts of glucosamine and omega-3-fatty acid to an arthritic joint so as to reduce the severity of symptoms of arthritis. In addition to tablets and capsules, suitable formulations of the oral therapeutic composition include, but are not limited to, pastes, gels, elixir, and lozenges. The therapeutic composition may also be in the form of a nasal or oral spray, a suppository, eye drops and ear drops, a topical patch, a systemic implant, or as a formulation for systemic injection or injection into an affected joint.

The therapeutic composition comprises an amount of glucosamine and omega-3-fatty acid which is effective to reduce the symptoms of arthritis. The ratio of glucosamine to omega-3-fatty acid in the composition, on a weight to weight basis, may be 95:5 to 5:95, or any ratio in between. Generally, the ratio is between about 75:25 to about 25:75. In a preferred embodiment, the ratio of glucosamine to omega-3-fatty acid in the composition is about 60:40.

The concentrations of the glucosamine and omega-3-fatty acid components in the composition may vary depending on the desire of the user or dispenser of the composition. For example, a capsule containing the composition of the invention may comprise about 300 to 400 mg of glucosamine and about 200 to 300 mg of an omega-3-fatty acid. Alternatively, a capsule may contain about 150 to 200 mg of glucosamine and about 100 to 150 mg of omega-3-fatty acid. In the latter instance, in order to achieve an equivalent intraarticular concentration as with the first example, twice as many capsules would be administered. It is contemplated that capsules or tablets comprising the composition of the invention contain between 50 to 1000 mg of glucosamine and between 50 and 1000 mg of omega-3-fatty acid. However, if desired, the concentration of either or both components may be lower than 50 mg or higher than 1000 mg per tablet or capsule.

A similar situation with regard to concentration exists with formulations other than capsules or tablets. For example, a liquid formulation for oral administration or for injection may comprise about 300 to 400 mg of each of glucosamine and omega-3-fatty acid. A similar, but more dilute, liquid formulation may comprise about 150 to 200 mg of each component.

In addition to glucosamine and omega-3-fatty acid, the composition of the invention may comprise additional components, which additional components may not have a direct anti-arthritic effect. Such additional components may include a pharmaceutically acceptable carrier, such as water, alcohol, or buffered physiologic saline; and/or nutritional additives, such as vitamins like Vitamin E, minerals such as iron or selenium, amino acids, fats, and carbohydrates. Depending on the form of the composition, the composition may further comprise additional components such as preservatives, time-release agents, surfactants, gelling agents, or buffers.

The composition of the invention, comprising glucosamine and omega-3-fatty acid, in which composition glucosamine is preferably, but not necessarily, the sole chondroprotective agent, is administered to an animal in need of such therapy in an amount effective to control the symptoms of arthritis. Variables related to the amount of the composition to be administered include the severity of symptoms, the species of animal to be treated, and the body weight of the animal. Typically, the composition is administered in a dosage between about 0.5 to about 45 mg of the combined glucosamine and omega-3-fatty acid components per kilogram of body weight per day irrespective of species. The dosage may be administered, if desired, in divided doses, such as BID, TID, or QID.

The composition is administered for a time sufficient to reduce or control the symptoms of arthritis. One or two doses of the composition may be sufficient, or the composition may be administered on an as needed basis. Typically, the composition will be administered on an ongoing basis of several days to weeks or even months in duration.

The composition of the invention, comprising an omega-3-fatty acid component and a glucosamine component, is made by combining one or more omega-3-fatty acids, or a composition comprising one or more omega-3-fatty acids, with one or more glucosamines, or a composition comprising one or more glucosamines. The combining may be by any method which is suitable for combining therapeutic compounds, such as by mixing, distilling, dissolving, suspending, or blending. In a preferred embodiment, a powder containing a glucosamine is mixed with and dissolved in an oil containing an omega-3-fatty acid.

The following non-limiting examples are illustrative of the invention.

EXAMPLE 1

A composition in capsule form containing, per capsule, 250 mg of glucosamine hydrochloride, 75 mg of NAG, 135 mg of EPA, and 90 mg of DHA, is administered to dogs suffering from symptoms of arthritis at a dosage of about one capsule per 20 kg body weight BID for periods of time ranging from 3 days to 14 days. Improvement in clinical signs due to arthritis is observed to improve following one or two dosages, which improvement continues throughout the period of treatment.

EXAMPLE 2

A composition in tablet form containing, per tablet, 300 mg of glucosamine sulfate and 300 mg of EPA is administered to dogs suffering from symptoms of arthritis at a dosage of about one tablet per 20 kg body weight BID for periods of time ranging from 3 days to 14 days. Improvement in clinical signs due to arthritis is observed to improve following one or two dosages, which improvement continues throughout the period of treatment.

EXAMPLE 3

A composition in liquid suspension containing about 200 mg of glucosamine sulfate and about 200 mg of EPA per teaspoon (5 ml) is administered to human volunteers suffering from arthritis at a dosage of three teaspoons BID. The composition is judged to reduce the severity of symptoms of arthritis in the human volunteers.

EXAMPLE 4

The composition of Example 3, except that DHA is substituted in place of EPA and glucosamine hydrochloride is substituted in place of glucosamine sulfate, is administered to human volunteers as in Example 3. The composition is judged to reduce the severity of symptoms of arthritis in the human volunteers.

EXAMPLE 5

The composition of Example 1 is administered as in Example 1 for a period of one month to healthy dogs and to dogs suffering from arthritis. No harmful effects of the therapy is observed.

EXAMPLE 6

A composition in capsule form containing, per capsule, 325 mg of glucosamine sulfate, 135 mg of EPA, and 90 mg of DHA, is administered to dogs suffering from symptoms of arthritis at a dosage of about one capsule per 20 kg body weight BID for periods of time ranging from 3 days to 14 days. Improvement in clinical signs due to arthritis is observed to improve following one or two dosages, which improvement continues throughout the period of treatment.

EXAMPLE 7

A composition in capsule form is administered to human volunteers suffering from arthritis at a dosage of 600 mg EPA, 400 mg DHA, and 1500 mg glucosamine $SO_4$ BID. The composition is judged to be effective in reducing the severity of symptoms of arthritis.

EXAMPLE 8

A composition in capsule form containing, per capsule, 200 mg EPA, 100 mg DHA, and 100 mg glucosamine sulfate, is administered to dogs suffering from symptoms of arthritis at a dosage of about one capsule per 20 kg body weight BID for periods of time ranging from 3 days to 14 days. Improvement in clinical signs due to arthritis is observed to improve following one or two dosages, which improvement continues throughout the period of treatment.

EXAMPLE 9

A composition in capsule form containing, per capsule, 300 mg glucosamine sulfate, 75 mg EPA, and 25 mg DHA, is administered to dogs suffering from symptoms of arthritis at a dosage of about one capsule per 20 kg body weight BID for periods of time ranging from 3 days to 14 days. Improvement in clinical signs due to arthritis is observed to improve following one or two dosages, which improvement continues throughout the period of treatment.

EXAMPLE 10

A composition in capsule form containing, per capsule, 135 mg of EPA, and 90 mg of DHA, which composition is free of glucosamine, is administered to dogs suffering from symptoms of arthritis at a dosage of one capsule per 10 kg body weight BID for 10 days. No or minimal improvement in clinical signs due to arthritis is observed.

EXAMPLE 11

A composition in capsule form containing, per capsule, 250 mg of glucosamine hydrochloride and 75 mg of NAG, which composition is free of omega-3-fatty acid, is administered to dogs suffering from symptoms of arthritis at a dosage of one capsule per 10 kg body weight BID. No or minimal improvement in clinical signs due to arthritis is observed.

EXAMPLE 12

A composition in liquid suspension containing about 500 mg of chondroitin sulfate and about 200 mg of EPA and about 135 mg of DHA per teaspoon (5 ml) is administered to human volunteers suffering from arthritis at a dosage of three teaspoons BID. The composition is judged to reduce the severity of symptoms of arthritis in the human volunteers.

EXAMPLE 13

Clinical Case Histories in Dogs with Osteoarthritis

Example 13.1

A seven year old, 87 pound German Shepherd type dog with radiographically documented bilateral arthritis of the hips was treated twice daily for several months with a fish oil supplement containing 250 mg EPA and 167 mg DHA. The dog's owner reported little improvement on the fish oil regimen.

The fish oil regimen was replaced by BID administration of 153.5 mg EPA, 102.5 mg DHA, and 428 mg glucosamine. The owner reported that the dog's clinical signs greatly improved almost immediately. Specifically, the owner reported that, with the combination therapy of glucosamine and the omega-3-fatty acids, the dog showed great improvement in overall quality of life, decreased stiffness after inactivity, ability to walk, run, and jump.

The combination therapy was discontinued which resulted in a relapse of clinical signs. Clinical signs greatly improved upon resumption of the combination therapy. The dog has been on the combination therapy for several months, with continued relief from symptoms due to osteoarthritis and with no toxic effects from the therapy.

Example 13.2

A geriatric fourteen year old, 67 pound Labrador Retriever/Keeshond mixed breed dog with osteoarthritis was treated with 8 mg MEDROL®, (methylprednisolone acetate, Upjohn Co., Kalamazoo, Mich.), administered every other day for several years. Fish oil, containing 250 mg EPA and 167 mg DHA, was given SID for six months and then BID for two weeks in combination with the MEDROL®. The dog's owner noticed mild improvement on the therapy.

Glucosamine was then added to the treatment regimen at a dosage of 750 mg BID. After two weeks on this therapy, the owner reported great improvement in the dog's level of stiffness after inactivity, ability to walk and run, and overall quality of life.

Example 13.3

A ten year old, 80 pound Labrador Retriever/German Shepherd mixed breed dog with radiographically documented osteoarthritis of both elbows was treated BID for one week with 75 mg RIMADYL® (Carprofen, Pfizer, New York, N.Y.). The dog's owner reported some improvement on the RIMADYL® therapy.

The RIMADYL® was replaced by BID treatment with 115.3 mg EPA, 77 mg DHA, and 321 mg glucosamine $SO_4$. After two weeks on this therapy, the owner reported great improvement in the dogs level of stiffness after inactivity, ability to walk, run, and jump, and overall quality of life. The owner further reported that the results of this therapy were much better than that achieved with RIMADYL®.

The dog has since been maintained on the combination therapy for five months with a continuation of beneficial results and no noticeable deleterious effects.

Example 13.4

An eleven year old, 81 pound Old English Sheep Dog with osteoarthritis was treated for two weeks with a BID regimen of 234 mg EPA and 156 mg DHA. The dog's owner reported that the dog's clinical signs were somewhat improved.

750 mg of glucosamine was then added to each administration of EPA and DHA. After two weeks, the owner reported great improvement in level of stiffness after inactivity, ability to walk, run, and jump, and overall quality of life. The dog has been on the combination glucosamine/omega-3-fatty acid regimen for several months with no reduction in efficacy and no deleterious side effects.

Example 13.5

A nine year old, 48 pound Siberian Husky with radiographically diagnosed osteoarthritis of the left hip secondary to a surgically repaired acetabular fracture was maintained for several years on monthly injections of 100 mg of ADEQUAN®, during which time symptoms decreased in severity but persisted. A fish oil supplement containing 250 mg EPA and 167 mg DHA were added, with no noticeable improvement in response to the medications.

The treatment was stopped and replaced by a BID administration of 214 mg glucosamine, 77 mg EPA, and 51 mg DHA. The owner reported that the dog's condition markedly improved, and the dog became more active. The owner also stated that the dog had an easier time rising from a down position on this therapy than on the ADEQUAN®/omega-3-fatty-acid therapy. That is, the dog began to get up by pushing with its hind legs, rather than pulling itself up with its front legs, demonstrating a marked improvement in the arthritic hip.

Example 13.6

A ten year old, 85 pound German Shepherd mixed breed dog with severe osteoarthritis of the hips was treated with 750 mg BID glucosamine BID for two weeks. The owner reported no change in the dog's clinical signs.

The omega-3-fatty acids, 250 mg EPA and 167 mg DHA, were then added to each administration of the glucosamine for two weeks. After this time, the owner reported improvement in the dog's level of stiffness after inactivity, ability to walk, run, and jump, and overall quality of life. The owner also stated that the beneficial results of this therapy were superior to those obtained during prior intermittent administration of MEDROL®.

Example 13.7

A six year old, 22 pound Scottish Terrier with osteoarthritis of the knee had been treated without success with a combination of aspirin and shark cartilage supplement. The aspirin was discontinued and replaced by 25 mg RIMADYL®. The RIMADYL® and the shark cartilage were continued for three months with some amelioration of clinical signs.

At that time, the RIMADYL® was stopped and was replaced by 107 mg glucosamine, 38.5 mg EPA, and 28.5 mg DHA which were administered BID with the shark cartilage. The owner reported that, on this regimen, there was great improvement in the dog's ability to walk and run normally, which improvement was reported to be better than that obtained with the RIMADYL®.

Example 13.8

An eleven year old, 64 pound German Shepherd/Labrador Retriever mix breed dog with severe osteoarthritis of the elbows was treated with 650 mg aspirin BID with minimal relief of symptoms. Treatment with aspirin was stopped and replaced with BID administration of 321 mg glucosamine, 115.3 mg EPA, and 77 mg DHA. The owner reported that results with the glucosamine/omega-3-fatty acid combination were superior to those obtained with aspirin.

As shown in the above examples, combination therapy with glucosamine and omega-3-fatty acid, with or without additional anti-arthritis compounds, provides relief from the symptoms of arthritis in dogs, an animal model for arthritis in other species, such as humans. The relief obtained with the combination therapy according to the invention is comparable to, and typically is equal or superior to, the relief which is obtained with conventional therapies, such as aspirin, corticosteroids, or non-steroidal anti-inflammatory drugs, without the potentially toxic side effects of these therapies.

Further modifications, uses, and applications of the invention described herein will be apparent to those skilled in the art. It is intended that such modifications be encompassed in the following claims.

I claim:

1. A composition for the treatment of arthritis comprising glucosamine, or a polymer or copolymer thereof, and omega-3-fatty acid, in amounts effective to elicit a synergistic response.

2. The composition of claim 1 which contains no chondroprotective agent other than glucosamine, or a polymer or copolymer thereof.

3. The composition of claim 1 which contains no anti-inflammatory agent other than omega-3-fatty acid.

4. The composition of claim 1 wherein the glucosamine and the omega-3-fatty acid are the sole components of the composition which are effective in treating symptoms of arthritis.

5. The composition of claim 1 wherein the glucosamine is selected from the group consisting of glucosamine sulfate, glucosamine hydrochloride, and N-acetyl glucosamine.

6. The composition of claim 1 wherein the omega-3-fatty acid is selected from the group consisting of eicosapentaenoic acid (EPA) and docosahexaenoic acid (DHA).

7. The composition of claim 1 wherein the ratio of the glucosamine and the omega-3-fatty acid is between 75:25 and 25:75 on a weight to weight basis.

8. The composition of claim 1 wherein the composition is in a formulation selected from the group consisting of tablet, capsule, paste, gel, elixir, lozenge, spray, suppository, drops, patch, systemic implant, and oral or injectable solution or suspension.

9. The composition of claim 1 which further comprises a pharmaceutically acceptable carrier.

10. The composition of claim 1 which further comprises Vitamin E.

11. A method for treating arthritis in animals comprising administering to an animal suffering symptoms of arthritis synergistically effective amounts of glucosamine and omega-3-fatty acid, and continuing the administration of the composition until the symptoms of arthritis are reduced.

12. The method of claim 11 wherein the animal is a mammal selected from the group consisting of humans, dogs, cats, horses, and cattle.

13. The method of claim 11 wherein the administration is oral.

14. The method of claim 11 wherein the administration is by injection.

15. The method of claim 11 wherein the glucosamine is selected from the group consisting of glucosamine sulfate, glucosamine hydrochloride, and N-acetyl glucosamine.

16. The method of claim 11 wherein the omega-3-fatty acid is selected from the group consisting of eicosapentaenoic acid (EPA) and docosahexaenoic acid (DHA).

17. The method of claim 11 wherein the composition is in a formulation selected from the group consisting of tablet, capsule, paste, gel, elixir, lozenge, spray, suppository, drops, patch, systemic implant, and oral or injectable solution or suspension.

18. The method of claim 11 wherein the glucosamine and the omega-3 fatty acid are administered as a single composition.

19. The method of claim 11 wherein the ratio of the glucosamine and the omega-3-fatty acid is between 75:25 and 25:75 on a weight to weight basis.

20. A method for making a composition for the treatment of arthritis in animals comprising combining a glucosamine and an omega-3-fatty acid in amounts effective to elicit a synergistic response.

21. The method of claim 20 wherein the combining is by mixing a powder comprising glucosamine and an oil comprising omega-3-fatty acid.

22. The method of claim 20 wherein, prior to the combining, the glucosamine is present in a composition which is substantially free of omega-3-fatty acid.

23. The method of claim 20 wherein, prior to the combining, the omega-3-fatty acid is present in a composition which is substantially free of glucosamine.

24. The method of claim 20 wherein, prior to the combining, the glucosamine is present in a composition which comprises purified glucosamine.

25. The method of claim 20 wherein, prior to the combining, the omega-3-fatty acid is present in a composition which comprises purified omega-3-fatty acid.

26. The method of claim 20 wherein the ratio of the glucosamine and the omega-3-fatty acid is between 75:25 and 25:75 on a weight to weight basis.

27. The method of claim 20 wherein the glucosamine is selected from the group consisting of glucosamine sulfate, glucosamine hydrochloride, and N-acetyl glucosamine.

28. The method of claim 20 wherein the omega-3-fatty acid is selected from the group consisting of eicosapentaenoic acid (EPA) and docosahexaenoic acid (DHA).

* * * * *